United States Patent
Okunishi et al.

(10) Patent No.: US 10,888,574 B2
(45) Date of Patent: Jan. 12, 2021

(54) METHOD FOR SUPPRESSING OBESITY, METHOD FOR TREATING OBESITY, AND METHOD FOR PROMOTING GENE EXPRESSION

(71) Applicant: Kinjirushi Co., Ltd., Aichi (JP)

(72) Inventors: Isao Okunishi, Aichi (JP); Tomoe Kato, Aichi (JP)

(73) Assignee: KINJIRUSHI CO.. LTD., Nagoya (JP)

( * ) Notice: Subject to any disclaimer, the term of this patent is extended or adjusted under 35 U.S.C. 154(b) by 0 days.

(21) Appl. No.: 16/146,507

(22) Filed: Sep. 28, 2018

(65) Prior Publication Data

US 2019/0099437 A1    Apr. 4, 2019

(30) Foreign Application Priority Data

Oct. 2, 2017    (JP) ................. 2017-192807

(51) Int. Cl.
*A61K 31/7048* (2006.01)
*A61P 3/04* (2006.01)

(52) U.S. Cl.
CPC ............ *A61K 31/7048* (2013.01); *A61P 3/04* (2018.01)

(58) Field of Classification Search
CPC .............................. A61K 31/7048; A61P 3/04
USPC ........................................................ 514/23
See application file for complete search history.

(56) References Cited

U.S. PATENT DOCUMENTS

| | | | |
|---|---|---|---|
| 2004/0006128 A1* | 1/2004 | Bibbs | A61P 3/10 514/456 |
| 2008/0146657 A1 | 6/2008 | Tsuboi et al. | |
| 2009/0156657 A1 | 6/2009 | Naito et al. | |
| 2009/0265865 A1 | 10/2009 | Lockridge et al. | |
| 2015/0201661 A1* | 7/2015 | Heuer | A61K 36/899 424/750 |

FOREIGN PATENT DOCUMENTS

| | | |
|---|---|---|
| JP | 2011518829 A | 6/2011 |
| JP | 2013035858 A | 2/2013 |
| JP | 2016185922 A | 10/2016 |
| WO | 2005042508 A1 | 5/2005 |

OTHER PUBLICATIONS

Yamasaki et al. Anti-obesity effects of hot water extract from Wasabi (*Wasabia japonica Matsum.*) leaves in mice fed high-fat diets. Nutrition Research and Practice (Nutr Res Pract) 2013;7(4):267-272. (Year: 2013).*
Nagai et al. The effect of isosaponarin isolated from wasabi leaf on collagen synthesis in human fibroblasts and its underlying mechanism. J Nat Med (2010) 64:305-312. (Year: 2010).*
Rahbar et al. The Hypolipidemic Effect of Citrullus colocynthis on Patients with Hyperlipidemia. Pakistan Journal of Biological Sciences 13 (24): 1202-1207, 2010. (Year: 2010).*
Al-Snafi AE. Chemical constituents and pharmacological effects of Citrullus colocynthis—A review. IOSR Journal of Pharmacy vol. 6, Issue 3 (Mar. 2016), pp. 57-67. (Year: 2016).*
Delazar et al. Flavone C-Glycosides and Cucurbitacin Glycosides From Citrullus Colocynthis. Daru vol. 14, No. 3, p. 109-114, 2006. (Year: 2006).*

* cited by examiner

*Primary Examiner* — Yih-Horng Shiao
(74) *Attorney, Agent, or Firm* — Westman, Champlin & Koehler, P.A.; Z. Peter Sawicki; Amanda M. Prose

(57) ABSTRACT

The present disclosure relates to a method for suppressing obesity, which includes administering to a subject a compound represented by the following formula

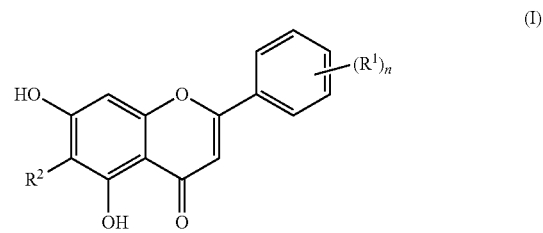

wherein n is an integer of 1 to 5; when n is 1, $R^1$ is —OH or —O-glycosyl; when n is an integer of 2 to 5, one $R^1$ is —OH and the other $R^1$(s) is/are —O-glycosyl; and $R^2$ is -glycosyl.

5 Claims, 2 Drawing Sheets
Specification includes a Sequence Listing.

SEQUENCE LISTING

<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: Synthetic DNA

<400> SEQUENCE: 1
gcctgcctag cagacatcat                                           20

<210> SEQ ID NO 2
<211> LENGTH: 19
<212> TYPE: DNA
<213> ORGANISM: Artificial
<220> FEATURE:
<223> OTHER INFORMATION: Synthetic DNA

<400> SEQUENCE: 2
tggccttcac cttggatct                                            19

<210> SEQ ID NO 3
<211> LENGTH: 22
<212> TYPE: DNA
<213> ORGANISM: Artificial
<220> FEATURE:
<223> OTHER INFORMATION: Synthetic DNA

<400> SEQUENCE: 3
aatgtatccg ttgtggatct ga                                        22

<210> SEQ ID NO 4
<211> LENGTH: 21
<212> TYPE: DNA
<213> ORGANISM: Artificial
<220> FEATURE:
<223> OTHER INFORMATION: Synthetic DNA

<400> SEQUENCE: 4
gcttcaccac cttcttgatg t                                         21

METHOD FOR SUPPRESSING OBESITY, METHOD FOR TREATING OBESITY, AND METHOD FOR PROMOTING GENE EXPRESSION

CROSS-REFERENCE TO RELATED APPLICATIONS

This application claims the benefit of Japanese Patent Application No. 2017-192807 filed on Oct. 2, 2017 with the Japan Patent Office, the entire disclosure of which is incorporated herein by reference.

BACKGROUND

The present disclosure relates to a method for suppressing obesity, a method for treating obesity, and a method for promoting gene expression.

Obesity refers to a state in which fat is excessively accumulated in the body. When energy intake exceeds energy expenditure, surplus energy is converted into fat and accumulated in adipose tissues. In order to increase energy expenditure, it is effective to increase thermogenesis by activating the body's basal metabolism. A large influence is exerted on the body's basal metabolism by mitochondrial uncoupling protein (UCP). The UCP has a function of uncoupling oxidative phosphorylation reaction in the internal membrane of mitochondria to release energy as heat.

For example, Japanese Unexamined Patent Application Publication No. 2016-185922 discloses a UCP1 gene expression enhancer containing piceatannol as a conventional technique for modulating gene expression of the UCP1, which is a typical UCP.

SUMMARY

The present inventors searched for a component that enables activation of energy metabolism to thereby suppress obesity in a manner different from conventional ones.

The present disclosure has been made under such circumstances, and it is desirable to provide a method for suppressing obesity, a method for treating obesity, and a method for promoting gene expression, which could activate energy metabolism.

The present disclosure relates to a method for suppressing obesity, which comprises administering to a subject a compound represented by the following formula (I).

The present disclosure relates to a method for treating obesity, which comprises administering to a subject, with a view to treating obesity, a compound represented by the following formula (I).

The present disclosure relates to a method for promoting gene expression, in which UCP1 gene expression is promoted, the method comprising administrating to a subject a compound represented by the following formula (I):

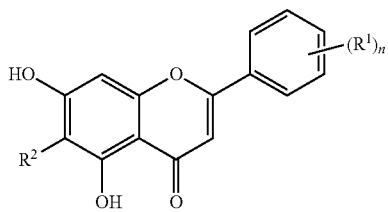

(I)

In the formula (I), n is an integer of 1 to 5. When n is 1, $R^1$ is —OH or —O-glycosyl. When n is an integer of 2 to 5, one $R^1$ is —OH, and the other $R^1$(s) is/are —O-glycosyl. $R^2$ is -glycosyl.

BRIEF DESCRIPTION OF THE DRAWINGS

An example embodiment of the present disclosure will be described below by way of example with reference to the accompanying drawings, in which.

DETAILED DESCRIPTION OF THE PREFERRED EMBODIMENTS

Figure 1:
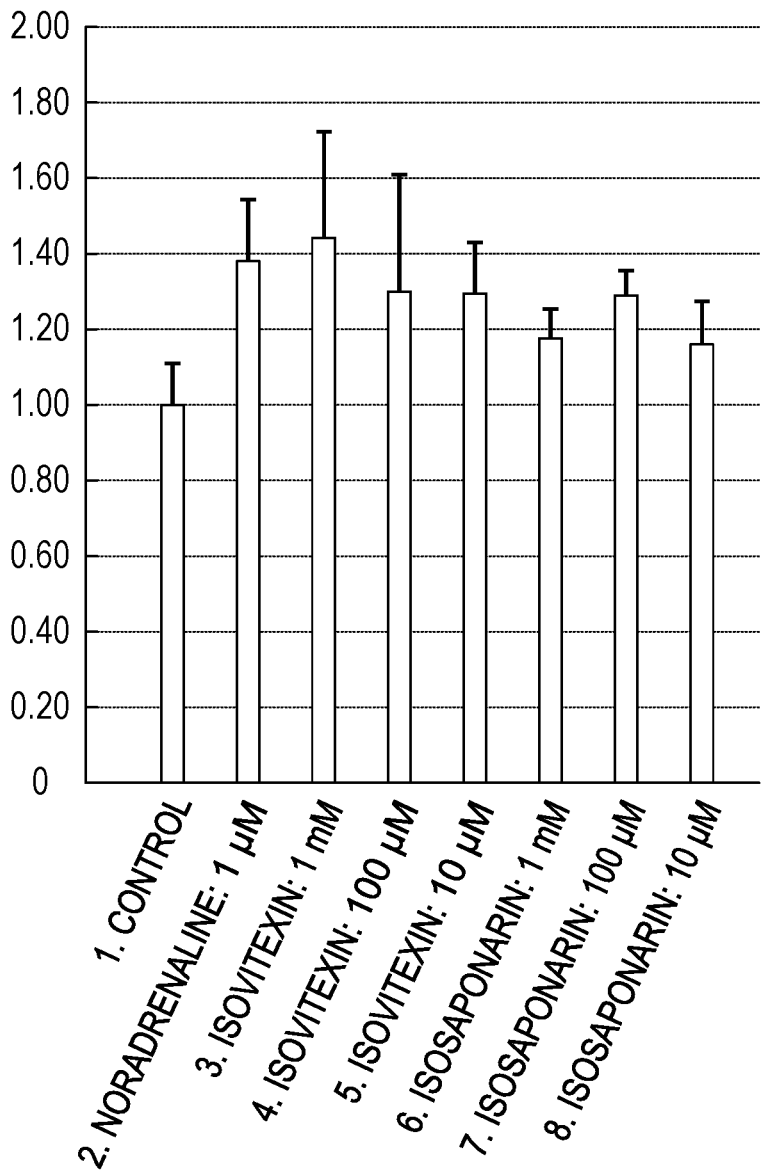
FIG. 1 is a diagram showing relative values of UCP1 gene expression.

An anti-obesity agent according to an embodiment of the present disclosure comprises a compound represented by the following formula (I):

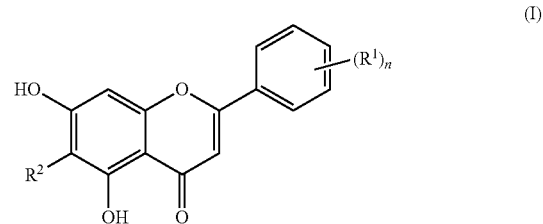

(I)

In the formula (I), n is an integer of 1 to 5. Preferably, n is 1 or 2. When n is 1, $R^1$ is —OH or —O-glycosyl (an example of —O-glycosyl is —O-glucosyl). When n is an integer of 2 to 5, one $R^1$ is —OH, and the other $R^1$(s) is/are —O-glycosyl. $R^2$ is -glycosyl (an example of -glycosyl is -glucosyl).

When $R^1$ is —O-glycosyl, it is preferred that the -glycosyl be one or two sugars selected from the group consisting of glucose, rhamnose, fructose, and galactose. The -glycosyl may be either monosaccharide or polysaccharide; however, monosaccharide is preferred.

$R^2$ is -glycosyl. The -glycosyl is preferably one or more sugars selected from the group consisting of glucose, rhamnose, fructose, and galactose, and is more preferably glucose. The -glycosyl may be either monosaccharide or polysaccharide; however, monosaccharide is preferred.

In $R^1$ and $R^2$, monosaccharide refers to a sugar comprising a monosaccharide molecule, and polysaccharide refers to a sugar chain with two or more monosaccharide molecules linked together. It is preferred that the polysaccharide be formed with two or more and ten or less monosaccharides linked together, and it is further preferred that the polysaccharide be formed with two or more and five or less monosaccharides linked together. $R^2$ may be the same as or different from $R^1$.

In the present embodiment, it is preferred that the compound be represented by the following formula (II):

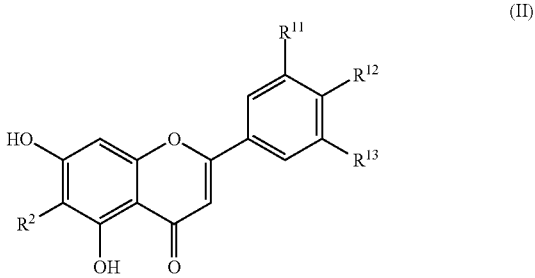

(II)

In the formula (II), $R^{12}$ is —OH or —O-glycosyl. When $R^{12}$ is —OH, $R^{11}$ and $R^{13}$ are —H. When $R^{12}$ is —O-glycosyl, $R^{11}$ and $R^{13}$ are both —H, or one of them is —OH and the other is —H. $R^2$ is -glycosyl.

In the present embodiment, it is preferred that the compound be represented by the following formula (III) or (IV):

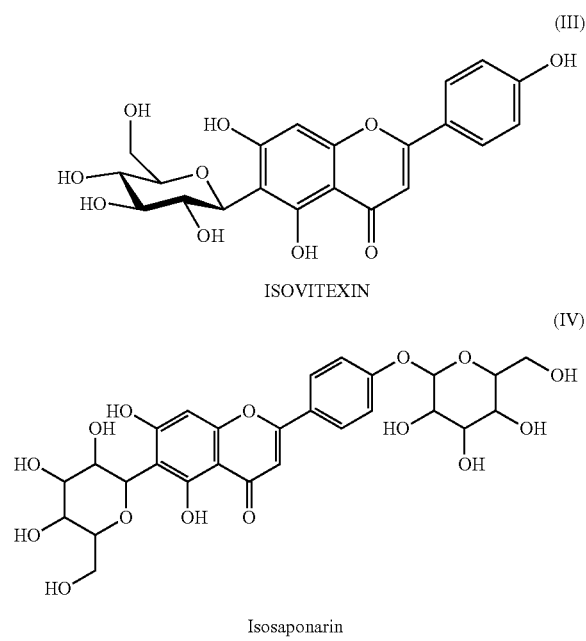

ISOVITEXIN

Isosaponarin

The compounds represented by the above formulae (I) to (IV) are flavonoid compounds, and are each preferably flavonoid or a glycoside thereof, in particular. Conventionally, the compound represented by the formula (I) has been used as an antioxidant for hair dye (Published Japanese Translation of PCT International Publication No. 2011-518829), and has been used in an anti-inflammatory composition as an ingredient having antioxidant activity and antiarteriosclerotic action (Japanese Unexamined Patent Application Publication No. 2013-035858).

In the present embodiment, the flavonoid compound represented by the formula (I) is used as an active ingredient of the anti-obesity agent. The flavonoid compound of the present embodiment makes it possible to produce protein (e.g., UCP) involved in metabolic activation in large amount. The flavonoid compound of the present embodiment can suppress obesity by functioning as a metabolic activator that activates metabolism to thereby increase energy expenditure.

The flavonoid compound of the present embodiment is a component contained in many plants, such as herbs and buckwheat husks, and can be obtained by solvent extraction and chemical separation purification. The content of the flavonoid compound of the present embodiment in some plants amounts to several percent; thus, the flavonoid compound can be obtained easily. The solvent used for elution of the flavonoid compound may be water-based solvent and/or organic solvent, and the water-based solvent is preferably used. The water-based solvent is preferably water, ethanol, or methanol, and may be water alone or any mixed solution of water and lower alcohol, such as methanol and ethanol.

A dose of the anti-obesity agent of the present embodiment is decided by considering age, sex, body weight, usage, dosage, and so on of each patient. The usage may include, for example, oral administration. In the case of oral administration, a daily dose of the flavonoid compound in the anti-obesity agent is preferably 10 µg/day to 100 mg/day.

The anti-obesity agent of the present embodiment may further comprise an additive. For example, an excipient, a disintegrator, a binder, an antioxidant, a coating agent, a coloring agent, a corrigent, a surfactant, a plasticizer, and so on can be blended as the additive.

Moreover, an anti-allergic agent, a refrigerant, vitamins, and other crude drugs may also be blended with the anti-obesity agent of the present embodiment to the extent not reducing the effects of the present disclosure.

The anti-obesity agent of the present embodiment may be contained in foods, quasi-drugs, and drugs.

Forms of the foods containing the anti-obesity agent of the present embodiment may be chosen as desired, and are not limited. Specific forms of the foods may include, for example, general foods, general drinks, supplements, health foods, special purpose foods, foods with health claims such as foods with function claims and foods for specified health use, soft drinks, tea beverages, health drinks, alcoholic beverages such as wine, confectionery, cooked rice, bread, noodles, ready-prepared dishes, and seasonings.

The usage of the quasi-drugs and drugs containing the anti-obesity agent of the present embodiment may be chosen as desired, and is not limited. For example, the anti-obesity agent may be administered internally or externally.

The dosage forms of the drugs and quasi-drugs containing the anti-obesity agent of the present embodiment are not limited, and may include, for example, capsules, tablets, powders, granules, and solutions.

The anti-obesity agent and the compound represented by the above formula (I) of the present embodiment are suitable for the following applications:

a pharmaceutical composition for suppressing obesity comprising the anti-obesity agent, a food composition for suppressing obesity comprising the anti-obesity agent, a UCP1 gene expression promoter comprising the compound represented by the above formula (I), a therapeutic agent for obesity comprising the compound represented by the above formula (I), a method for suppressing obesity, which comprises administering the compound represented by the above formula (I) to the subject, a method for treating obesity, which comprises administering the compound represented by the above formula (I) to the subject with a view to treating obesity, a method for promoting UCP1 gene expression, which comprises administering the compound represented by the above formula (I) to the subject, use of a compound for manufacturing an anti-obesity agent intended to suppress obesity, the compound being represented by the above formula (II), use of a compound for manufacturing a therapeutic agent for obesity intended to treat obesity, the compound being represented by the above formula (II), use of a compound for manufacturing a UCP1 gene expression promoter that promotes UCP1 gene expression, the compound being represented by the above formula (I), a method for suppressing obesity, which comprises administering the anti-obesity agent to the subject, a method for suppressing obesity, which comprises administering a pharmaceutical composition for suppressing obesity to the subject, and a method for suppressing obesity, which comprises administering a food composition for suppressing obesity to the subject.

EXAMPLES

In each example, as described below, brown adipocytes were cultured in a test medium to which each of various test substances has been added, and then quantitative determination of expression level of UCP1 gene and quantitative determination of lipid droplets by Oil Red 0 staining were performed.

(1) Preparation of a Test Medium Containing a Test Substance

Noradrenaline is a substance known to bind to a β3 adrenergic receptor of a brown adipocyte and to activate the UCP1 gene by activating its signal transduction system to thereby increase thermogenesis (see, for example, International Publication No. WO 2005/042508). Noradrenaline is a reference object for UCP1 gene expression level when the following test substances were used. As the test substances, isovitexin and isosaponarin were used.

Noradrenaline used was product number A9512 manufactured by Sigma-Aldrich Co. LLC. Isovitexin used was product number 1235S manufactured by EXTRASYNTHESE. Isosaponarin used was a product manufactured by KINJIRUSHI Co., Ltd., lot number: 20110412, molecular weight: 594.5.

The media used were a growth medium (manufactured by Cosmo Bio Co., Ltd.), a differentiation-inducing medium (manufactured by Cosmo Bio Co., Ltd.), and a maintenance medium (manufactured by Cosmo Bio Co., Ltd.).

Noradrenaline, isovitexin, and isosaponarin were each added to the maintenance medium. The final concentration in each media was set to 1 µmol/L for noradrenaline; 1 mmol/L, 100 µmol/L, and 10 µmol/L for isovitexin; and 1 mmol/L, 100 µmol/L, and 10 µmol/L for isosaponarin.

(2) Culture of Brown Adipocytes

The brown adipocytes used in the test were those contained in the rat-derived primary brown adipocyte culture kit (manufactured by Cosmo Bio Co., Ltd., code number: BAT02). Using the above-described growth medium, the brown adipocytes were inoculated in the respective wells of a 24-well plate at a density of $3 \times 10^4$ cells/well. The brown adipocytes were cultured at 37° C. with 5% $CO_2$ for 3 days in a $CO_2$ incubator (multi-gas incubator, manufactured by Panasonic Healthcare Holdings Co., Ltd., product number: MCO-19MUVH). Next, the medium in each well was replaced with the differentiation-inducing medium, and culture was performed for 2 days in the $CO_2$ incubator (5% $CO_2$, 37° C.). Then, the medium in each well was replaced with the above-described maintenance medium, and culture was performed for 2 days in the $CO_2$ incubator (5% $CO_2$, 37° C.). Further, the medium in each well was replaced with the above-described maintenance medium again, and the brown adipocytes were cultured for 1 day in the $CO_2$ incubator (5% $CO_2$, 37° C.). Subsequently, analysis of gene expression and evaluation by Oil Red 0 staining were performed as below.

(3) Quantitative Determination of Expression Level of UCP1 Gene

RNAs were recovered from the brown adipocytes using 0.2 mL per well of TRI Reagent (manufactured by Molecular Research Center, Inc., catalog number: TR118). Using 500 ng of each sample RNA, cDNA synthesis was performed using a cDNA synthesis kit (product name: SuperScript [registered trademark] VILO™ cDNA Synthesis Kit, manufactured by Thermo Fisher Scientific Inc., catalog number: 11754050). Real-time PCR was performed using a real-time PCR kit (product name: LightCycler [registered trademark] Taqman [registered trademark] Master, manufactured by Roche Applied Science, catalog number: 4735536) and a real-time PCR device (product name: LigthCycler [registered trademark] 480 System II, manufactured by Roche Diagnostics). Analysis of UCP1 gene expression was performed using GAPDH as an internal standard.

Primers and probes used in the test were as follows:

UCP1 primer,
forward primer: gcctgcctagcagacatcat (SEQ ID No. 1, synthesized by Sigma-Aldrich Co. LLC),
reverse primer: tggccttcaccttggatct (SEQ ID No. 2, synthesized by Sigma-Aldrich Co. LLC),
probe: Universal ProbeLibrary probe #130 (manufactured by Roche Life Science Co. Ltd.),
GAPDH primer,
forward primer: aatgtatccgttgtggatctga (SEQ ID No. 3, synthesized by Sigma-Aldrich Co. LLC),
reverse primer: gcttcaccaccttcttgatgt (SEQ ID No. 4, synthesized by Sigma-Aldrich Co. LLC), and
probe: Universal ProbeLibrary probe #80 (manufactured by Roche Life Science Co. Ltd.).

The number of experiments performed was three. The results of relative expression level of UCP1 gene are shown in Table 1 and FIG. 1. Table 1 shows concentrations (final concentrations) of the respective test substances in the media, and average values, standard deviations (S.D.), and significant differences of relative values of UCP1 gene expression when the respective test substances were used. The significant difference is indicated as "<0.05" when the significance level of the t-test was 5%, and as "<0.01" when the significance level was 1%. FIG. 1 shows the average values and the standard deviations (S.D.) of the relative values of UCP1 gene expression when the respective test substances were used.

TABLE 1

| Test substance number | Ingredient Name of ingredient | Final concentration | Relative value of UCP1 gene expression Average | S.D. | Significant difference (two-sided t-test) |
|---|---|---|---|---|---|
| 1 | Control | | 1.00 | 0.11 | |
| 2 | Noradrenaline | 1 µmol/L | 1.38 | 0.16 | P < 0.05 |
| 3 | Isovitexin | 1 mmol/L | 1.45 | 0.28 | |
| 4 | | 100 µmol/L | 1.30 | 0.31 | |
| 5 | | 10 µmol/L | 1.30 | 0.13 | P < 0.05 |
| 6 | Isosaponarin | 1 mmol/L | 1.18 | 0.08 | |
| 7 | | 100 µmol/L | 1.30 | 0.06 | P < 0.05 |
| 8 | | 10 µmol/L | 1.17 | 0.11 | |

As shown in FIG. 1, when isovitexin or isosaponarin was used, significant increase in UCP1 gene expression was observed as compared with the case of the control. In particular, the rate of increase in UCP1 gene expression was significantly higher when the final concentration was 10 μmol/L in the group using isovitexin and when the final concentration was 100 μmol/L in the group using isosaponarin, than those of the other test substances.

The UCP1 gene encodes UCP1 (uncoupling protein 1), which is one of uncoupling proteins. The UCP1 is expressed specifically in brown adipocytes, and has a function of uncoupling oxidative phosphorylation in the mitochondria and releasing, as heat, the energy generated when the substrate is oxidized. It is known that, when mutation occurs in this gene, production of heat from the cell is reduced thus leading to an increased tendency to weight gain.

In the present examples, when isovitexin or isosaponarin was used, significant increase in UCP1 gene expression was observed as compared with the case of the control. Thus, it has been found that flavonoid compounds, such as isovitexin and isosaponarin, activate metabolism.

(4) Quantitative Determination of Lipid Droplets

Lipid droplets in the cell cultured as described in the above item (2) were quantitatively determined through the steps below using Lipid Assay Kit (manufactured by Cosmo Bio Co., Ltd., code number: AK09F).

Step 2-1. Fixative solution was prepared by mixing the following ingredients together:
37% formaldehyde solution (formalin stock solution): 100 mL,
purified water: 900 mL,
sodium dihydrogen phosphate monohydrate ($NaH_2PO_4 \cdot H_2O$): 4 g, and
disodium hydrogen phosphate, anhydrous ($Na_2HPO_4$): 6.5 g.

Step 2-2. The culture solution was removed from the well plate subjected to the culture operation in the above "(2) Culture of brown adipocytes". Then, each well was washed once with 500 μL per well of PBS.

Step 2-3. 500 μL per well of the fixative solution prepared in Step 2-1 was added to each well, and the well plate was left at rest overnight at room temperature. This resulted in immobilization of the cells on a wall of the well.

Step 2-4. After the immobilization, washing of each well with 500 μL per well of purified water was performed.

Step 2-5. Undiluted Oil Red 0 solution in the kit and purified water were mixed together at a ratio of 6:4 (volume ratio) to obtain a mixed solution, and the mixed solution was left at rest at room temperature for 10 to 15 minutes. Then, the mixed solution was filtered through a membrane filter having pores with a pore diameter of 0.5 to 1.0 μm. The filtrate was used as Oil Red 0 solution.

Step 2-6. 500 μL of the above-described Oil Red 0 solution was dispensed into each well, and the well plate was left at rest at room temperature for 15 minutes.

Step 2-7. After that, the Oil Red 0 solution was removed from the well, and each well was washed with purified water three times or more. Such washing was performed thoroughly until the used purified water becomes clear.

Step 2-8. 500 μL of solvent for extraction in the kit was added into the dried well, and pigments were eluted. 0.1 mL of the eluate with the pigments eluted therein was dispensed into each well of a 96-well plate, and absorbance at a wavelength of 540 nm was measured with a micro-plate reader (Infinite [registered trademark] M200 PRO, manufactured by TECAN). Assuming that the absorbance of the eluate in the case of the control is 100, the relative value of the absorbance of the eluate when each test substance was used was obtained by a formula below.

Relative value of the absorbance of the eluate when the test substance was used=100×Absorbance of the eluate when the test substance was used/ Absorbance of the eluate in the case of the control The relative value of the absorbance corresponds to the relative quantity of lipid droplets in the eluate when the test substance was used, assuming that the quantity of lipid droplets in the eluate in the case of the control is 100.

Figure 2:
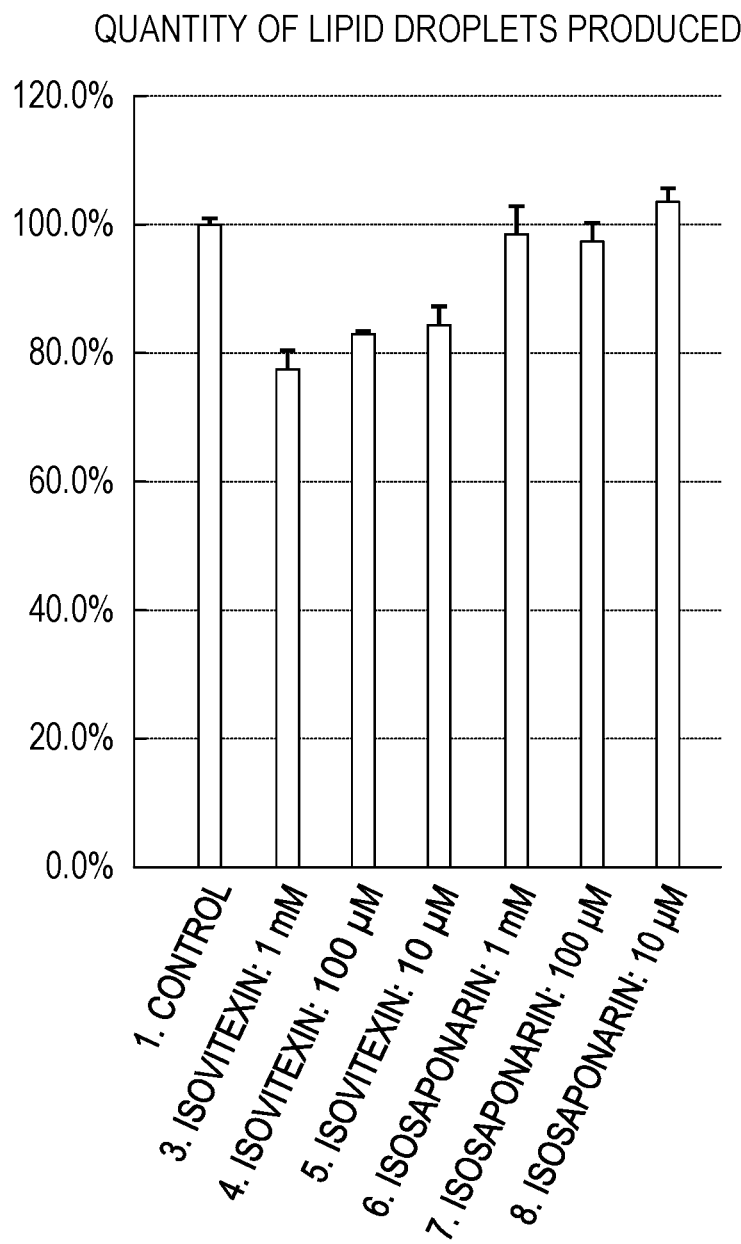
FIG. 2 is a diagram showing results of quantitative determination of lipid droplets.

The number of experiments performed was three. The results are shown in Table 2 and FIG. 2. Table 2 shows average values, standard deviations, and significant differences of the relative quantities of lipid droplets in the eluate when the respective test substances were used. The significant difference is indicated as "<0.05" when the significance level of the t-test was 5%, and as "<0.01" when the significance level was 1%. FIG. 2 shows the average values and the standard deviations (S.D.) of the relative values of UCP1 gene expression when the respective test substances were used.

TABLE 2

| Test substance number | Ingredient Name of ingredient | Concentration | Quantity of lipid droplets produced Average | S.D. | Significant difference (two-sided t-test) |
|---|---|---|---|---|---|
| 1 | Control | | 100.0% | 0.8% | |
| 3 | Isovitexin | 1 mmol/L | 77.8% | 2.6% | P < 0.01 |
| 4 | | 100 μmol/L | 83.3% | 0.2% | P < 0.01 |
| 5 | | 10 μmol/L | 84.8% | 2.7% | P < 0.01 |
| 6 | Isosaponarin | 1 mmol/L | 98.9% | 4.1% | |
| 7 | | 100 μmol/L | 97.7% | 2.7% | |
| 8 | | 10 μmol/L | 104.0% | 1.7% | P < 0.05 |

As shown in FIG. 2, when adipocytes were cultured in the medium to which isovitexin or isosaponarin has been added, the quantity of lipid droplets produced was smaller than in the case where adipocytes were cultured in the medium with no such substance is added thereto. In particular, the quantity of lipid droplets produced was significantly reduced in the case where the adipocytes were cultured in the medium containing isovitexin having the concentration of 10 μmol/L to 1 mmol/L and in the medium containing isosaponarin having the concentration of 10 μmol/L.

The examples of the anti-obesity agent have been described so far. However, the examples exemplified above can be modified variously. For example, the examples shown above are examples in which isovitexin or isosaponarin is used as an example of the flavonoid compound represented by the above formula (I); however, the present disclosure is not limited to this. Flavonoid compounds other than these can be used, and in such cases too, the effect of reducing the quantity of lipid droplets produced, which is similar to that in the case where isovitexin or isosaponarin was used, can be expected.

What is claimed is:

1. A method for suppressing obesity, the method comprising orally administering to a human subject in need thereof a composition:
   wherein the composition comprises an isosaponarin and at least one different additive selected from a group consisting of an excipient, a disintegrator, a binder, an antioxidant, a coating agent, a coloring agent, a corrigent, a surfactant, and a plasticizer, and
   a final concentration of the isosaponarin is set to 10 µmol/L in the step of administrating the composition to the human subject.

2. A method for treating obesity, the method comprising orally administering to a human subject in need thereof a composition,
   wherein the composition comprises an isosaponarin and at least one different additive selected from a group consisting of an excipient, a disintegrator, a binder, an antioxidant, a coating agent, a coloring agent, a corrigent, a surfactant, and a plasticizer,
   and a final concentration of the isosaponarin is set to 10 µmol/L in the step of administrating the composition to the human subject.

3. A method for promoting gene expression, in which UCP1 gene expression is promoted, the method comprising orally administrating to a human subject a composition,
   wherein the composition comprises an effective amount of isosaponarin and at least one different additive selected from a group consisting of an excipient, a disintegrator, a binder, an antioxidant, a coating agent, a coloring agent, a corrigent, a surfactant, and a plasticizer,
   and the effective amount of isosaponarin is obtained to significantly increase UCP1 gene expression compared with negative control.

4. The method for promoting gene expression according to claim 3,
   wherein a final concentration of the isosaponarin is set to 100 µmol/L in the step of administrating the composition to the human subject.

5. The method for promoting gene expression according to claim 3, wherein a final concentration of the isosaponarin is set to 10 µmol/L in the step of administrating the composition to the human subject.

* * * * *